(12) United States Patent
Steinmetz et al.

(10) Patent No.: US 8,748,665 B2
(45) Date of Patent: Jun. 10, 2014

(54) PROCESS FOR PREPARING AN AROMATIC AMINE AND APPARATUS THEREFOR

(75) Inventors: Tilmann Steinmetz, Gruenstadt (DE); Michael Nilles, Bobenheim-Roxheim (DE); Lucia Koenigsmann, Stuttgart (DE); Andreas Heussler, Hassloch (DE); Nikolaus Zafred, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 45 days.

(21) Appl. No.: 13/318,257

(22) PCT Filed: May 6, 2010

(86) PCT No.: PCT/EP2010/056209
§ 371 (c)(1),
(2), (4) Date: Oct. 31, 2011

(87) PCT Pub. No.: WO2010/128118
PCT Pub. Date: Nov. 11, 2010

(65) Prior Publication Data
US 2012/0083626 A1  Apr. 5, 2012

(30) Foreign Application Priority Data
May 7, 2009  (EP) ..................................... 09159617

(51) Int. Cl.
*C07C 209/00*  (2006.01)
(52) U.S. Cl.
USPC ....................................................... 564/420
(58) Field of Classification Search
None
See application file for complete search history.

(56) References Cited

U.S. PATENT DOCUMENTS 6,716,352 B1  4/2004  Livingston

FOREIGN PATENT DOCUMENTS

| DE | 10 2006 008 000 | 11/2006 |
| EP | 0 507 118 | 10/1992 |
| GB | 666 544 | 2/1952 |
| GB | 2 352 715 | 2/2001 |

OTHER PUBLICATIONS

Machine Translation of DE-10200600800, 2006, pp. 1-8.*
U.S. Appl. No. 13/320,384, filed Nov. 14, 2011, Koenigsmann, et al.
International Search Report Issued Oct. 19, 2010 in PCT/EP10/056209 Filed May 6, 2010.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

The invention relates to a process for obtaining at least one aromatic amine from a liquid mixture comprising water and the at least one aromatic amine by extracting with at least one nitroaromatic in an extraction column (1) to form an essentially water- comprising raffinate stream and an extract stream comprising the at least one nitroaromatic and the aromatic amine. The extraction column (1) is divided by a dividing wall (3) into two regions (5, 7), and, in the case of an amount of liquid for separation which is less than a minimum cross sectional loading of the entire extraction column (1), the liquid mixture to be separated is fed only to one of the regions (5, 7) of the extraction column (1) divided by the dividing wall (3). The invention further relates to a process for preparing an aromatic amine and to an apparatus for separating a liquid mixture comprising water and at least one aromatic amine by extracting with at least one nitroaromatic, comprising an extraction column (1).

12 Claims, 4 Drawing Sheets

PROCESS FOR PREPARING AN AROMATIC AMINE AND APPARATUS THEREFOR

Figure 1:
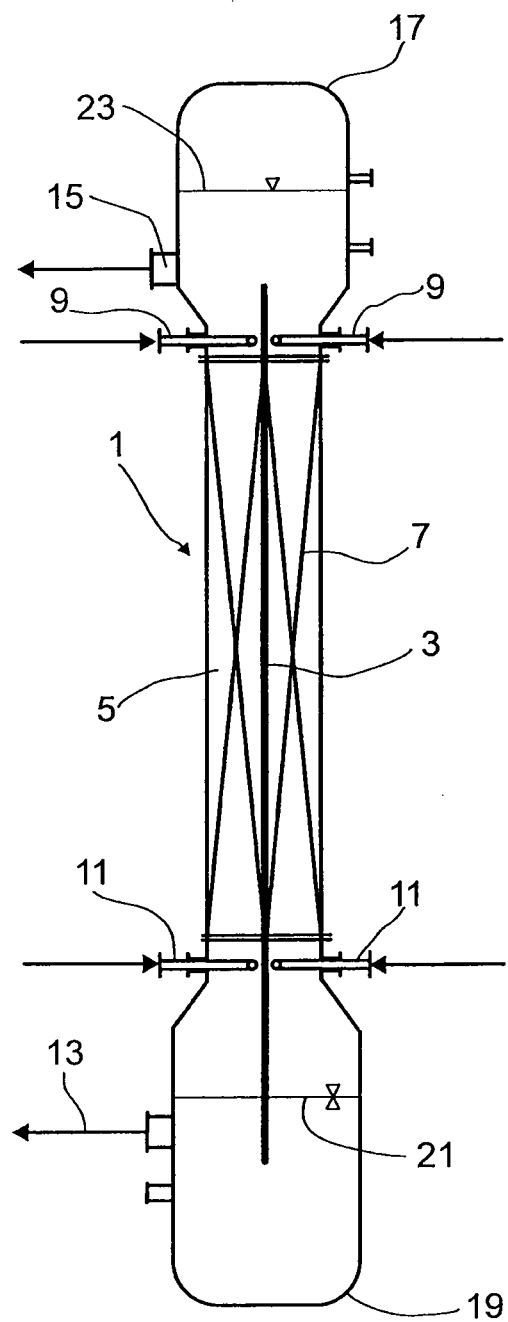

The invention relates to a process for preparing at least one aromatic amine by extracting a liquid mixture comprising water and the at least one aromatic amine with at least one nitroaromatic in an extraction column to form an essentially water-comprising raffinate stream and an extract stream comprising the at least one nitroaromatic and the aromatic aniline. The invention further relates to a process for preparing aromatic amines by catalytically hydrogenating the corresponding nitroaromatic and to an apparatus for separating a liquid mixture comprising water and at least one aromatic amine by extracting with at least one nitroaromatic, comprising an extraction column.

The liquid mixture which comprises water and the aromatic amine and is to be separated by the extraction originates generally from a process for preparing aromatic amines by hydrogenating the corresponding nitroaromatic in the presence of a heterogeneous catalyst. Such a process for preparing aromatic amines is described, for example, in EP-B 0 507 118.

Preference is given to using the nitroaromatic used to prepare the aromatic amine as a solvent in the extraction to obtain the aromatic amine. The extraction forms an extract phase comprising the aromatic amine and the nitroaromatic, which is separated in a subsequent separating stage, for example a distillation, into the aromatic amine as the product of value and a stream comprising essentially the nitroaromatic. The nitroaromatic thus removed can then likewise be passed as a reactant into the reactor for preparing the aromatic amine.

One example of a process for obtaining an aromatic amine from an aqueous phase by extracting the aromatic amine with a corresponding nitroaromatic is known from DE-A 10 2006 008 000. The solvent used for the extraction is preferably the nitroaromatic used to prepare the aromatic amine. In the course of extraction, the aromatic amine dissolves in the nitroaromatic and can then be removed therefrom by a distillative separation.

For the extraction, common extraction apparatus known to the person skilled in the art is used, for example mixer/settlers or extraction columns. However, a disadvantage of common extraction columns is that they require liquid loadings at a particular level to develop the specified separating performance in operation. If, however, large variations in the feed occur, this can lead to widening of partial load vortices, which is associated with an excessively low liquid loading and a deterioration in the extraction performance up to and including nonattainment of the raffinate concentration. When aniline is used as the aromatic amine, this results in aniline black formation in the downstream stage.

It is an object of the present invention to provide a process and an apparatus for obtaining aromatic amine from a liquid mixture comprising water and the at least one aromatic amine by extraction, which can also be operated with highly variable volume flows of the liquid mixture which comprises water and aromatic amine and is to be separated, without loss of separating performance.

The object is achieved by a process for obtaining at least one aromatic amine from a liquid mixture comprising water and the at least one aromatic amine by extracting with at least one nitroaromatic in an extraction column to form an essentially water-comprising raffinate stream and an extract stream comprising the at least one nitroaromatic and the aromatic amine, wherein the extraction column is divided by a dividing wall into two regions, and, in the case of an amount of liquid for separation which is less than a minimum cross sectional loading of the entire extraction column, the liquid mixture to be separated is fed only to one of the regions of the extraction column divided by the dividing wall.

"Essentially water-comprising raffinate stream" in the context of the present invention means that the raffinate stream comprises at least 98% by weight of water, more preferably at least 99.5% by weight of water, especially at least 99.99% by weight of water.

The upper operating limit of an extraction column is determined by the flood point and sets the maximum column load. The maximum column load is typically 75 to 80% below the flood point load, which reflects the operating point at maximum cross sectional loading of the extraction column. A higher maximum column load is typically not set since the risk of reaching an unstable operating point is too great in the event of variations in the feed streams, temperatures or concentrations.

The lowermost load limit of an extraction column is typically about 50% partial load, which typically corresponds to a load of about 40% of the flood load. At such low loads, however, it is well known that backmixing in columns with random packing increases significantly. In addition, the liquid distributors with which the liquids are added to the extraction column have only a narrow working range in which the droplet sizes required can be obtained. The inventive dividing wall can reduce the cross section of the extraction column. Typically, the dividing wall is in the middle of the column, such that the cross section is halved. This makes it possible to operate the extraction column with a very much lower load. In the case of operation of only one of the regions divided by the dividing wall, a cross sectional loading comparable to the maximum column load of the overall extraction column is already achieved at half load. This allows the operating range of the extraction column to be widened significantly compared to an extraction column without a dividing wall.

The dividing wall in the extraction column thus makes it possible, even in the case of a small liquid stream to be separated, to be able to perform an extraction without any great loss of separating performance. For example, enlargement of vortices which occur in the extraction column is also prevented by the dividing wall and reduced by the dimensions to the cross section between column wall and dividing wall. The vortices which form at partial load of the extraction column, the size of which is the diameter of the column, lead to an increase in backmixing. Backmixing generally worsens the separating performance based on the column height, the effect of which is that the height of the column has to be increased. The dividing wall allows the construction height of the extraction column to be selected at a lower level for a very wide load range than the necessary construction height for the same load range without the dividing wall.

A further advantage of the process according to the invention is that, even in the case of operation of two reactors for preparing the at least one aromatic amine, only one extraction column is required in order to process the liquid mixture which comprises water and aromatic amine and forms in the reaction. Even in the case of operation of only one of the reactors which are connected to the extraction column, sufficient separating action is achieved for a sufficiently pure aromatic amine as the product.

The extraction column used may be any extraction column known to those skilled in the art. Suitable columns have internals, typically in the form of structured or unstructured packings. In particular, unstructured packings are used, generally random packings. Suitable random packings are any random packings known to those skilled in the art. Especially suitable random packings are, for example, Pall rings.

The structured packing in the extraction column is positioned between the first feed at the top and the second feed at the lower end of the column. The use of packings achieves homogeneous liquid distribution in the extraction column, or in the region of the extraction column in operation.

In a first embodiment, the dividing wall ends below the liquid level in the extraction column and above a first feed apparatus at the top of the extraction column. By virtue of the dividing wall ending below the liquid level in the extraction column, the liquid from both regions of the extraction column divided by the dividing wall is collected in a common head. This has the advantage that only one fill level measuring device need be present at the top of the column. Even in the case of operation of only a subregion of the extraction column, irrespective of the region in operation, regulation can be performed with only one liquid level measuring device.

It is additionally advantageous when the dividing wall penetrates the phase boundary which forms. It is additionally preferred when the bottom of the extraction column is likewise not divided for the two regions divided by the dividing wall. As a result, it is likewise sufficient to provide all measuring apparatus needed for the regulation of the extraction at the bottom of the column only once. There is no need to consider the two subregions separately.

The fact that the dividing wall projects into the liquid phase to be removed in the bottom of the extraction column means that the lower end of the dividing wall is below a phase boundary between the liquid phase to be removed and the phase comprising all liquids used in the extraction.

In order to operate only one region of the extraction column in the case that the dividing wall does not run from end to end, it is advantageous to leave liquid standing in the second region.

In order to prevent a loop flow from arising around the dividing wall between the active region and the inactive region owing to the hydrostatic pressure difference existing on the basis of the different mean densities in the two regions of the extraction column which are formed by the dividing wall, it is necessary that the dividing wall projects into the liquid phase to be removed in the bottom of the extraction column to such an extent that the different position of the phase boundary between the liquid phase to be removed and the extraction mixture which comprises all components does not lead to the continuous phase flowing under or over the dividing wall.

The height difference of the phase boundaries $h_{sep}$ can be estimated via the densities of the phases, the expected holdup $\phi$ and the level of the half of the column $H_{act}$ operated under biphasic conditions, as follows:

$$h_{sep} = \phi \cdot \frac{|(\rho_c - \rho_d)|}{\rho_d} \cdot H_{act}.$$

Alternatively, loop flow around the dividing wall can also be prevented by virtue of the dividing wall concluding, for example, either with the tray at the bottom of the extraction column, thus also dividing the bottom of the extraction column into two regions, or projecting to beyond the maximum liquid level of the extraction column at the top and, for example, also being connected to the lid of the extraction column which closes it at the top. Alternatively, it is also possible that the dividing wall divides the entire extraction column into two separate regions. If either the bottom or the top is, or else bottom and top of the extraction column are, divided into two separate regions by the dividing wall, it is necessary in each case to provide separate inlets into and outlets from the individual subregions of the extraction column. For instance, in the case of separation of the bottom into two regions, two separate bottom outlets have to be provided for removal of the liquid phase to be removed at the bottom of the liquid. In the case of separation of the liquid phase present in the top of the extraction column, it is necessary to provide a withdrawal stub in each of the regions in order to withdraw the liquid which collects at the top of the extraction column. In the case of a corresponding division into separate regions, it is also necessary to provide dedicated measuring apparatus in each region in order to be able to control and regulate the extraction. For this reason, it is preferred when both the liquid present at the top of the column and the liquid present at the bottom of the column are not divided by the dividing wall.

Owing to the differences in density of the liquids, the extraction column is typically operated such that an essentially water-comprising raffinate stream is withdrawn at the top of the column. "Essentially water-comprising" means, in the context of the present invention, that the raffinate stream withdrawn at the top of the column comprises at least 98% by weight, preferably at least 99.5% by weight and especially at least 99.99% by weight of water.

Accordingly, the liquid phase to be removed in the bottom of the extraction column is an essentially anhydrous extract phase comprising the at least one nitroaromatic and the at least one aromatic amine. Essentially anhydrous means, in the context of the present invention, that the extract phase is free of extraneous phases or comprises not more than 1% by weight of an extraneous phase. When the extract phase is free of extraneous phases, this means that the proportion of water in the extract phase corresponds to no more than the proportion which dissolves in the extract phase owing to temperature and pressure.

In order to operate the extraction column, depending on the amount of liquid mixture which comprises water and aromatic amine and which is to be separated, either completely or only in one of the regions divided by the dividing wall, a first feed opens into the upper region of the extraction column and a second feed opens at the lower end of the column above the bottom in each of the regions divided by the dividing wall.

The nitroaromatic which serves as the solvent is typically supplied through the first feed at the top of the column. The liquid mixture which comprises water and the at least one aromatic amine and is to be separated is supplied as feed via the second feed at the lower end of the column above the bottom. The supply of feed and solvent at opposite ends of the column achieves countercurrent flow of solvent and feed.

In order to be able to operate the individual regions of the extraction column separately, it is additionally necessary to be able to supply the separate feeds into the individual regions of the extraction column separately with the liquids to be introduced into the extraction column. For this purpose, it is possible, for example, to be able to close the individual feeds by means of suitable valves in each case. The valves are preferably controllable as a function of the total amount of water to be separated and the liquid mixture comprising at least one aromatic amine.

In order to prevent the same liquid from standing in the second region of the extraction column over a long period in the case of prolonged operation of only one region of the extraction column, it is additionally preferred, in this case, to switch operation between the regions at regular intervals.

The nitroaromatic used to obtain the aromatic amine is preferably nitrobenzene and the aromatic amine is preferably aniline.

The invention further relates to a process for preparing aromatic amines by catalytically hydrogenating the corresponding nitroaromatic, comprising the following steps:

(a) converting a reaction mixture comprising the nitroaromatic and hydrogen in the presence of a heterogeneous catalyst to give a product mixture comprising the aromatic amine, water and unconverted hydrogen in an equilibrium reaction, (b) removing the hydrogen from the product mixture, (c) dewatering the product mixture to obtain an essentially anhydrous aromatic amine as the product, and a liquid mixture comprising water and residues of the aromatic amine, (d) separating the liquid mixture which comprises water and residues of the aromatic amine and is obtained in step (c) in a process as described above by extracting with a nitroaromatic to give a raffinate stream comprising essentially water and an extract stream comprising the nitroaromatic and the aromatic aniline.

By using the above-described process for extracting the liquid mixture comprising the water and the aromatic amine in step (d), it is possible, depending on the aromatic amine required, to conduct the preparation process at different loads. It is also possible, for example, to connect two separate apparatuses for performing the preparation process to only one extraction column and alternatively only to operate one of the two reaction lines or both reaction lines.

A suitable reactor which is used to prepare the aromatic amine is any reactor which is known to those skilled in the art and is suitable for the hydrogenation of nitroaromatic to aromatic amine. Reactors used customarily are, for example, fluidized bed reactors in which the heterogeneous catalyst used for the reaction is present as fluidized granules. In such a fluidized bed reactor, the reaction is performed in the gas phase. For this purpose, preferably both the hydrogen and the nitroaromatic are added in gaseous form. Alternatively, it is, however, also possible to add the nitroaromatic in liquid form and to evaporate it in the reactor. Preference is given, however, to gaseous addition.

To control the reaction temperature, it is possible to provide a heat transferer in the fluidized bed reactor, which can supply heat to the endothermic reactions or remove heat in the case of exothermic reactions. The heat transferer may have a plate or tubular configuration and be arranged vertically, horizontally or in an inclined manner in the fluidized bed reactor. A suitable heat carrier flows through the tubes or plates of the heat transferer.

In addition to a fluidized bed reactor, examples of suitable reactors are, however, also a tubular reactor or a reaction column which comprise the catalyst. In this case, the catalyst is preferably installed into the reaction column or the tubular reactor in the form of a packing.

Suitable catalysts for the hydrogenation of the nitroaromatic to the aromatic amine are the known particulate, supported or unsupported catalysts which are used to hydrogenate aromatic amines. Especially suitable are catalysts which comprise heavy metals of the first and/or fifth to eighth group of the Periodic Table. The catalyst preferably comprises one or more of the elements copper, palladium, molybdenum, tungsten, nickel and cobalt.

In order to obtain very substantially complete conversion of the nitroaromatic used, it is preferred to conduct the reaction with a hydrogen excess. Since the product mixture which forms in the reaction is generally in gaseous form and generally still comprises the unreacted hydrogen, it is necessary, in a next step, first to remove the hydrogen from the product mixture. For this purpose, preference is given to using a condenser in which the aromatic amine and the water condense out. The gaseous constituents, especially the hydrogen, are removed. The hydrogen which is still present in gaseous form and is removed in the condensation of the aromatic amine and the water is preferably recycled into the reaction. In order to remove any gaseous inerts present from the process, it is additionally possible to discharge a portion of the unreacted hydrogen from the process. This can, for example, be purified and then likewise recycled into the reaction. Alternatively, it is, however, also possible, for example, to utilize the hydrogen, for example, as a fuel.

After the removal of the hydrogen from the product mixture comprising the aromatic amine, water and the unconverted hydrogen, the remaining product mixture comprising aromatic amine and water is worked up to obtain the aromatic amine as the product. For this purpose, the product mixture is dewatered to obtain an essentially anhydrous aromatic amine as the product and a liquid mixture comprising water and residues of the aromatic amine. The dewatering is effected, for example, by a liquid/liquid phase separation. The phase separation can be performed in any desired apparatus suitable for liquid/liquid phase separation. In addition to a liquid/liquid phase separation, it is, however, also possible to use any other suitable process known to those skilled in the art to dewater the product mixture comprising aromatic amine and water.

The dewatering gives rise to a liquid mixture which comprises water and residues of the aromatic amine, and an organic phase which comprises the desired aromatic amine as the crude product. The amount of the aromatic amine in the liquid mixture comprising the water and the residues of the aromatic amine depends on the pressure and temperature-dependent solubility of the corresponding aromatic amine in water. Based on aniline as the aromatic amine, the liquid mixture comprising water and residues of the aromatic amine comprises, at atmosphere pressure and room temperature, generally 0.5 to 15% by weight, preferably 1 to 10% by weight and more preferably 3 to 5% by weight of aniline, with or without small amounts of by-products.

The phase comprising the aromatic amine as the crude product is purified to obtain a pure aromatic amine, generally by processes known to those skilled in the art. For example, it is possible for this purpose to work up the product comprising the aromatic amine further in a distillation. In this case, the aromatic amine is typically obtained as the top stream, and residues present in the product are removed at the bottom of the column.

The distillation can be performed in any distillation apparatus known to those skilled in the art. Typically, a distillation column is used for this purpose. Suitable distillation columns generally have internals, for example in the form of trays, structured packings or unstructured packings. Examples of suitable trays in a distillation column are bubble-cap trays, sieve trays or valve trays. Structured packings typically used are commercially available and are sold, for example, under the Mellapak® name by Sulzer. The unstructured packings used are generally random packings. In order that the random packings remain in the distillation column and do not fall through it, a grid tray is typically used, on which the random packings rest. Suitable random packings which can be used in the distillation column are known to those skilled in the art. Random packings typically used are, for example, Pall rings, Raschig rings, Berl saddles or Intalox saddles. However, it is also possible to use any other form of random packings known to those skilled in the art. Customary materials from which the random packings are manufactured are, for example, metals, ceramics or plastics. When selecting the material, it should be ensured merely that it is inert toward the media to be separated in the distillation.

The desired product purity of the product stream essentially comprising the aromatic amine can be achieved by a suitable distillation regime. For example, it is possible to perform a multistage distillation. Alternatively, it is also possible to configure the distillation column with an appropriate number of theoretical plates. A further means of increasing the product purity of the product stream is to provide an evaporator at the bottom of the distillation column and to evaporate at least some of the bottom stream and recycle it into the distillation column.

The aromatic amine is extracted from the liquid mixture comprising the water and residues of the aromatic amine by the process described above. The extraction is effected with a nitroaromatic, especially with the nitroaromatic used as the reactant for the reaction. In the course of the extraction, the aromatic amine dissolves in the nitroaromatic and forms an extract phase comprising the nitroaromatic and aromatic amine. The water freed of the aromatic amine leaves as the raffinate phase.

In a preferred embodiment of the process according to the invention for preparing aromatic amines, the nitroaromatic used as the solvent in step (d) is the nitroaromatic used to prepare the aromatic amine. This prevents contamination by a further nitroaromatic in the course of extraction. It is unnecessary to use an additional substance.

A further advantage of the use of the nitroaromatic used to prepare the aromatic amine as the solvent in the extraction is that, after the extraction, the nitroaromatic can be supplied as the reactant to the reaction for preparing the aromatic amine in step (a). For this purpose, it is preferred when the extract stream obtained in step (d) is recycled into the reactor. In this way, the aromatic amine present in the extract stream is also recycled into the reactor and thus passes again into the dewatering and can be obtained as the product. In this way, the aromatic amine removed in the extraction is likewise obtained as the product of value in the process and is not discharged from the process with the nitroaromatic as the extractant. Recycling into the reactor additionally has the advantage that no further workup of the extract stream is necessary.

The further object is achieved by an apparatus for separating a liquid mixture comprising water and at least one aromatic amine by extracting with at least one nitroaromatic, comprising an extraction column, which extraction column is divided by a dividing wall into two regions, and control means are additionally provided, with which the extraction can be regulated such that, in the case of an amount of liquid for separation which is less than the minimum cross sectional loading of the entire extraction column, the liquid mixture to be separated is fed only to one of the regions of the extraction column divided by the dividing wall.

Control means are understood to mean, in particular, suitable sensors for detecting operating states, for example fill level meters, flow meters, temperature sensors and pressure sensors, and suitable regulators for regulating valves or other controllable and regulable units. Typically, a regulating unit by means of which it is possible to intervene manually into the process and which displays the relevant parameters is also included. Parameters which are detected are especially the liquid level in the extraction column, the position of the phase boundary of the liquid to be removed, inflows and outflows of components, and the ratio of supplied to separated liquid mixture to supplied solvent. These parameters can be used to establish, for example, the liquid level, flow rates of the liquids supplied and mass or volume flows of the liquids withdrawn. With reference to the amount of liquids supplied, it is additionally possible to assess whether only one region or both regions of the extraction column divided by the dividing wall should be operated.

The dividing wall in the extraction column allows in each case only one of the regions divided by the dividing wall to be operated, while the other region is idle. Since the dividing wall does not necessarily divide the entire extraction column, but rather, more particularly, regions in the bottom and in the top of the extraction column are not divided by the dividing wall, even when only one of the regions of the extraction column divided by the dividing wall is in operation, liquid is present in the other region. For this reason, the dividing wall, as already described above, should be configured such that loop flow is avoided. This can be achieved, for example, by virtue of the dividing wall projecting into the liquid phase to be removed in the bottom of the extraction column. In this case, the lower boundary of the dividing wall projects to such an extent into the liquid phase to be removed that the different position of the phase boundary between the liquid phase to be removed and the extraction mixture which comprises all components does not lead to the continuous phase flowing under or over the dividing wall.

Flow around the dividing wall can alternatively be prevented by virtue of the dividing wall ending below the liquid level in the extraction column and above a first feed apparatus at the top of the extraction column.

The solvent is typically supplied via the first feed apparatus at the top of the extraction column. In the lower region of the column, the mixture to be separated is introduced into the extraction column via a second feed apparatus. The solvent and the mixture to be separated are thus conducted in countercurrent in the extraction column.

In order to be able to operate each of the regions divided by the dividing wall independently of one another, a first feed opens into the upper region of the extraction column and a second feed opens at the lower end of the column above the bottom in each of the regions divided by the dividing wall. It is then possible in each case to add the solvent through the first feed and the mixture to be separated through the second feed.

Alternatively, it is, however, also possible, for example, to provide a common distributor for both regions, but, for example, to be able to close, by means of valves, the part of the distributor through which liquid is supplied into a region in each case and keep the other open. In this way, it is possible to use a common distributor in each case to supply either a region or else the entire extraction column with liquid.

Suitable distributors are any distributors known to those skilled in the art. Suitable distributors are configured, for example, in the form of pipelines which branch off from a main distributor, in which case exit orifices are provided in the individual pipelines, through which the liquid to be supplied can emerge. Alternatively, it is, however, also possible, for example, to use ring distributors or similar distributors known to those skilled in the art.

Working examples of the invention are shown in the drawings and are explained in detail in the description which follows.

Figure 2:
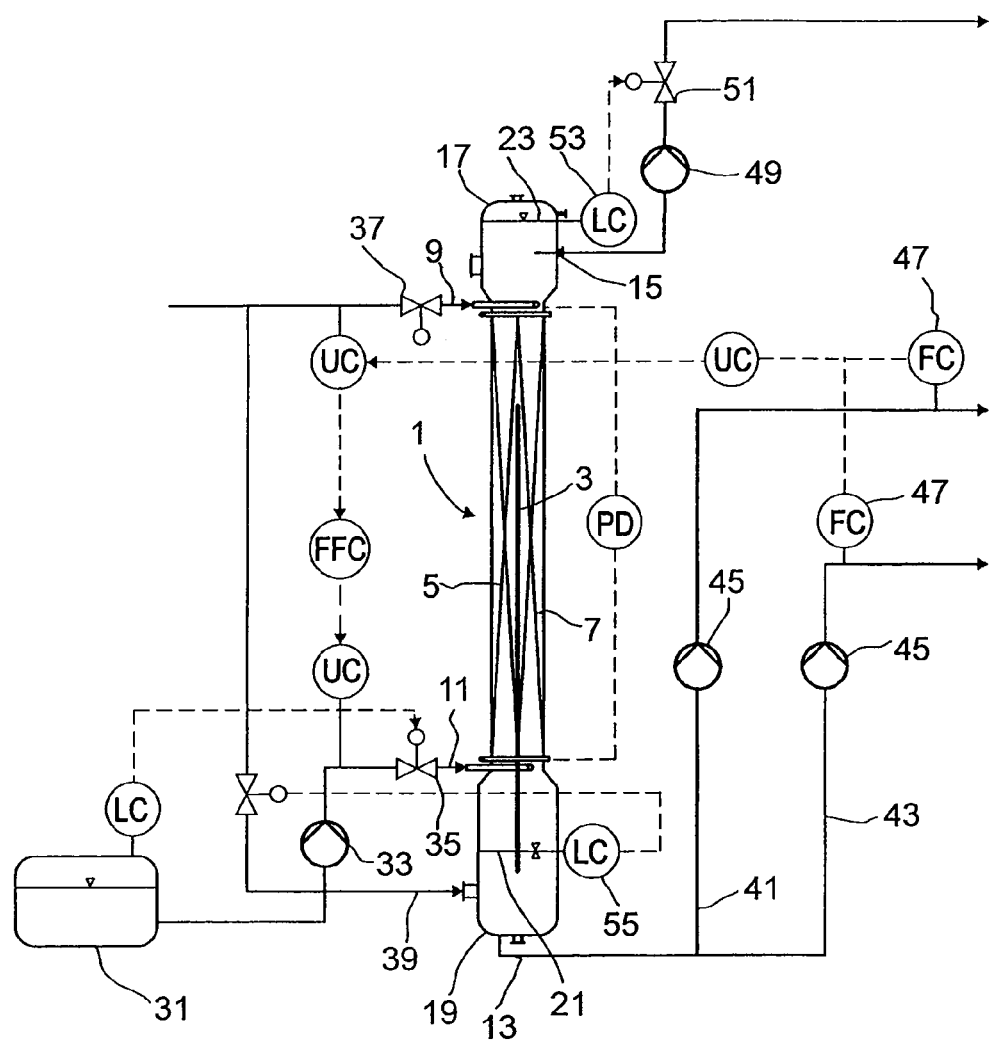
Figure 3:
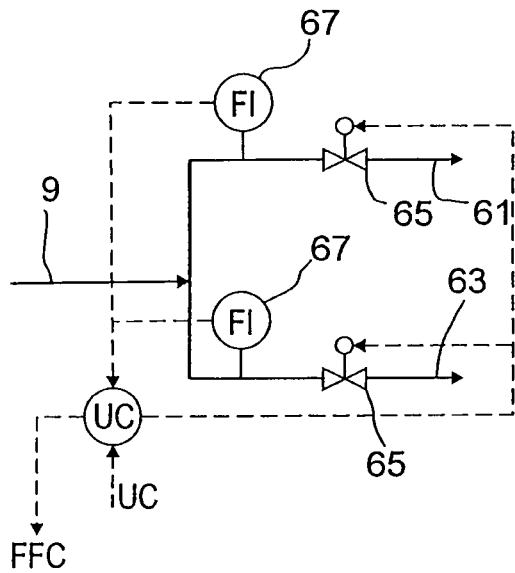
Figure 4:
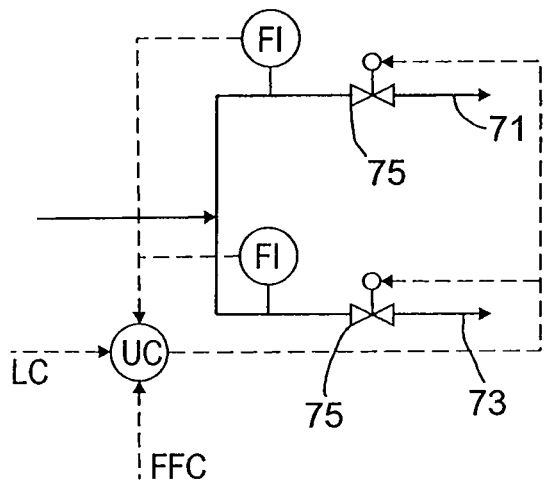
Figure 5:
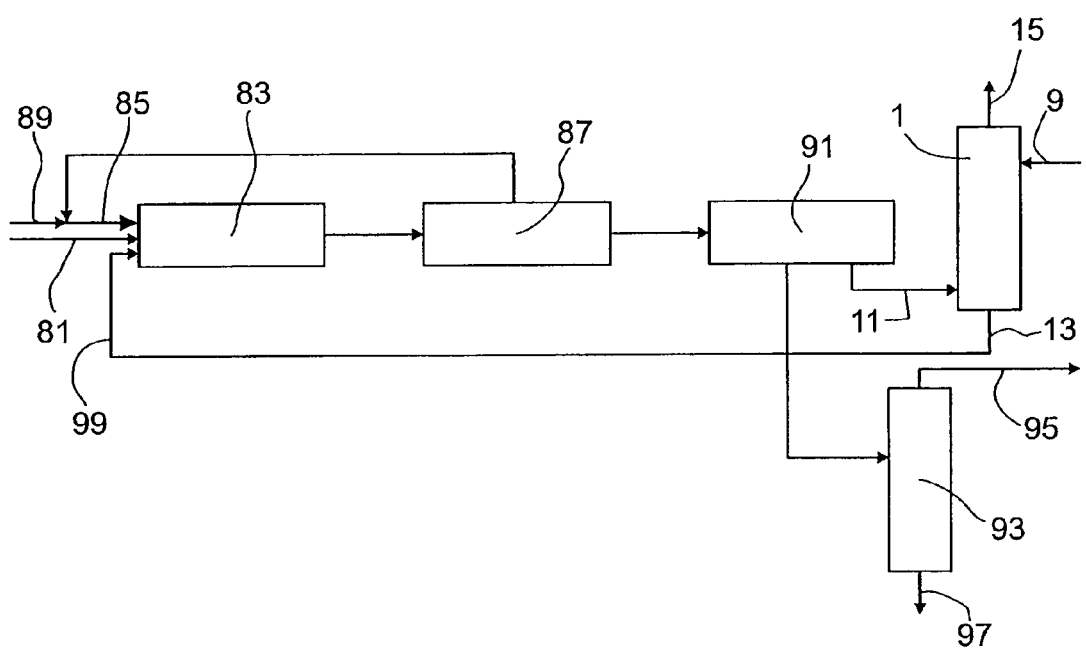

The figures show:

FIG. 1 an extraction column configured in accordance with the invention,

FIG. 2 a process flow diagram of the extraction process,

FIG. 3 a detailed diagram of the solvent feed,

FIG. 4 a detailed diagram of the feed of the liquid mixture to be separated, FIG. 5 a schematic diagram of the process for preparing the aromatic amine.

FIG. 1 shows an extraction column configured in accordance with the invention.

An extraction column 1 configured in accordance with the invention is divided by a dividing wall 3 into a first region 5 and a second region 7. The first region 5 and the second region 7 are preferably of identical construction. The dividing wall 3 is preferably also positioned such that the regions 5, 7 are of equal size.

In each of the two subregions 5, 7, a first feed 9 opens out in the upper region of the extraction column 1. The solvent is supplied through the first feed 9. In order to be able to operate the first subregion 5 and the second subregion 7 separately from one another, independent first feeds 9 into the first region 5 and the second region 7 are provided. The first feeds 9 into the first region 5 and the second region 7 are preferably of identical configuration. In order to be able to operate the first region 5 and the region 7 independently of one another, the first feeds 9 open into the extraction column 1 below the upper conclusion of the dividing wall 3.

Alternatively, it is, however, also possible, for example, to provide only one first feed 9 for supply of the solvent, though it is also necessary with a single first feed 9 to ensure that the first subregion 5 and the second region 7 can be operated separately from one another. For this purpose, in this case, it is possible, for example, to configure the first feed 9 such that the feed into the first region 5 or into the second region 7 can be closed in each case by means of shutoff elements, for example valves.

A liquid mixture to be separated is supplied to each of the regions 5, 7 via a second feed 11 at the lower end of the extraction column 1. In the context of the present invention, the liquid mixture to be separated is a mixture which comprises water and aromatic amine. The second feed 11 is configured just like the first feed 9, such that both the first region 5 and the second region 7 can be supplied independently with the liquid mixture to be separated. Supply of both regions 5, 7 with the liquid mixture through the second feed 11 is also possible. For this purpose, in the same way as for the first feed 9, it is possible that two separate second feeds 11 are provided in each of the regions 5, 7, but a conceivable alternative is a single second feed 11, in which the distributors into the first region 5 or into the second region 7 are each closable by means of suitable shutoff elements, for example valves, such that the first region, the second region 7 or both regions 5, 7 can be operated.

For better dispersion and to prolong the residence time of the liquid mixture to be separated with the solvent, suitable internals are provided in each case in the first region 5 and in the second region 7. Suitable internals are especially structured or unstructured packings, especially unstructured packings. Unstructured packings refer typically to random packings. Random packings which can be used in the context of the present invention are, for example, Pall rings, Raschig rings, saddles or any other random packings which are suitable for extraction and are known to those skilled in the art.

In order to achieve sufficient extractive action, the first feeds 9 are preferably positioned above the internals present in the regions 5, 7. The second feeds 11 through which the liquid mixture to be separated is added are preferably arranged below the internals in the regions 5, 7. In order to enable operation of the individual regions 5, 7, the dividing wall is configured such that the feeds 9, 11 each open into the regions 5, 7 divided by the dividing wall 3 in the extraction column 1, even if the dividing wall 3, as shown in FIG. 1, does not divide the entire extraction column 1.

A dividing wall 3 which does not divide the entire extraction column, as shown, for example, in FIG. 1, is preferred, since this enables provision of only one liquid outlet 13 at the bottom of the column and a second liquid outlet 15 at the top of the column. In the case of complete separation into two regions, a separate liquid outlet at the bottom and at the top would be needed for each region. In addition, in the case of complete division of the extraction column 1, it would also be necessary to provide all necessary measurement and regulation units in both regions. In the case of a dividing wall 3, as shown in FIG. 1, however, single measurement and regulation units in each case at the top 17 and at the bottom 19 of the extraction column 1 are sufficient.

An essentially water-comprising stream, from which the aromatic amine has been extracted, is withdrawn via the second liquid outlet 15 at the top 17 of the extraction column 1. At the bottom 19 of the extraction column 1, the nitroaromatic used as the solvent with the aromatic amine dissolved therein collects. Between the liquid phase to be removed, which comprises the nitroaromatic and the aromatic amine, and the liquid mixture to be extracted, which additionally also comprises the water, a phase boundary 21 develops. In order to enable independent operation of the first region 5 and of the second region 7, it is necessary that the dividing wall 3 ends below the phase boundary 21 in the liquid mixture to be removed, which is drawn off via the liquid outlet 13 at the bottom 19 of the extraction column 1. In this case, the dividing wall 3 must project into the liquid phase to be removed to such an extent that loop flow is prevented in the case of operation of only one of the regions 5, 7.

The extraction column 1 is typically operated in such a way that it is not completely filled with liquid. The liquid level in the extraction column 1 is indicated by reference numeral 23 in the embodiment shown here.

FIG. 2 shows a flow diagram of the extraction process.

A liquid mixture which comprises water and aromatic amine and is to be separated is collected in a reservoir vessel 31. The liquid mixture comprising water and aromatic amine originates, for example, from a process for preparing aromatic amine from the corresponding nitroaromatic. In the reservoir vessel 31, the liquid mixture comprising water and aromatic amine from one or more processes for preparing the aromatic amine can be collected. For example, it is possible to work up the liquid mixture comprising aromatic amine and water from several processes in only one extraction column 1. Since, in this case, however, depending on the required production rate of the aromatic amine, under some circumstances, only some of the processes are operated, it is necessary to be able to operate the extraction column 1 over a wide load range. For this purpose, the extraction column 1 is divided by the dividing wall 3 into two regions 5, 7. In this way, it is possible to operate only one of the regions 5, 7 or both regions 5 and 7. This allows operation of the extraction column 1 over a very wide load range, such that, even when, for example, two processes for preparing the aromatic amine are provided, satisfactory separation is achieved when only one of the two processes for preparing the aromatic amine is operated. In addition to the reservoir vessel 31, it will be appreciated that it is alternatively also possible that the extraction column 1 is supplied directly with the liquid mixture comprising aromatic amine and water from the process for preparing the aromatic amine.

In the embodiment shown here, the liquid mixture comprising the water and the aromatic amine is supplied to the extraction column 1 with a pump 33 via the second feed 11 in the lower region of the extraction column 1. The amount of liquid to be supplied can be controlled by means of a valve 35.

The solvent, especially the nitroaromatic also used to prepare the aromatic amine, is supplied via the first feed 9 in the upper region of the extraction column 1. In order to adjust the amount of the nitroaromatic to be supplied, a regulating valve 37 is provided.

To monitor operation, the position of the phase boundary 21 is monitored. As soon as the position of the phase boundary 21 goes below a lower value, it is possible to supply solvent into the bottom via a feed 39. This allows the amount of liquid to be removed at the bottom 19 of the extraction column to be increased, and the phase boundary 21 to be shifted upward. This is necessary especially in the case of operation of only one of the regions 5, 7, in order to prevent the phase boundary 21 from going below the lower end of the dividing wall 3, in order that no loop flow arises.

The liquid phase to be removed, which comprises the nitroaromatic as the solvent and the aromatic amine dissolved therein, is drawn off through the liquid outlet 13 at the bottom 19 of the extraction column 1. In a preferred embodiment, the extract stream is supplied as the reactant to the preparation of the aromatic amine. In the embodiment shown here, the liquid outlet 13 is divided into two separate lines 41, 43, each of the lines 41, 43, for example, opening into a reactor for preparation of the aromatic amine. In order to be able to operate the reactors separately, a pump 45 is incorporated into each of the lines 41, 43. The pump 45 can be used to transport the extract stream into the reactor connected to the line 41, 43 in each case, via the particular line 41 or 43. A flow meter 47 is used in each case to measure the reactant stream withdrawn via each of lines 41, 43. It is also possible in this way to regulate the amount of the nitroaromatic to be supplied.

The essentially water-comprising stream, from which the aromatic amine has been extracted, is withdrawn via the second liquid outlet 15 at the top 17 of the extraction column 1. The amount of the raffinate withdrawn via the second liquid outlet 15 is adjusted, for example, by means of a pump 49 and a regulating valve 51. The pump 49 serves especially to transport the raffinate stream and the regulating valve 51 to set the amount to be withdrawn. More particularly, the pump 49 and the regulating valve 51 can also be used to adjust the liquid level 23 in the extraction column 1. The liquid level 23 is monitored with a suitable fill level meter 53.

Owing to the dividing wall 3 which does not run from end to end, it is sufficient in each case to provide a fill level meter 53 at the top of the column and a liquid level meter 55 with which the position of the phase boundary 21 is monitored. In the case of complete separation, it would be necessary to provide such a fill level meter 53 or liquid level meter 55 in each of the regions of the extraction column 1 divided by the dividing wall 3.

In order to ensure error-free operation of the extraction column, it is additionally advantageous to regulate the flow ratio between feed of mixture to be separated and solvent. This is typically effected by means of the valves 35, 37. It is also advantageous to monitor the pressure difference over the internals in the extraction column 1.

FIG. 3 shows, in detail, the first feed 9 through which the solvent is added. In order to be able to operate the first region 5 and the second region 7 of the extraction column independently of one another, it is necessary to be able to supply solvent both to the first region 5 and to the second region 7 independently of one another. In a preferred embodiment, which is shown here, the first feed 9 is therefore divided into a feed 61 into the first region 5 of the extraction column 1 and a second feed 63 into the second region 7 of the extraction column 1. The feed 61 into the first region 5 and the feed 63 into the second region 7 may each independently be closed or opened by a valve 65. With the valve 65 open, solvent flows through the particular feed 61, 63 into the extraction column; with the valve 65 closed, the particular feed is closed. In this way, it is possible to independently operate the first region 5, the second region 7 or both regions at the same time. For monitoring, a liquid display 67 is provided in each of the feeds 61, 63. One regulation parameter used is the flow rate of the extract stream withdrawn from the process.

FIG. 4 shows, in detail, the feed of the liquid mixture to be separated. The liquid mixture to be separated is supplied via a feed 71 to the first region of the extraction column and via a feed 73 to the second region of the extraction column. Each of the feeds 71, 73 incorporates a valve 75 to adjust the amount of liquid which is to be supplied through the particular feed 71, 73 to the extraction column 1. It is also possible, when the operation of only one region 5 or 7 is intended, to close the feed 71 or 73 which opens into the region 5 or 7 which is not in operation in the extraction column 1. In the same way as for the solvent supply, this is also necessary in order to enable independent operation of the first region 5 or of the second region 7. The valves 75 are regulated firstly via the flow ratio between feed of solvent and feed of mixture to be separated, and also via the fill level of the reservoir vessel 31. In order to be able to control the valves 75 correspondingly, the flow ratio, the flow through the particular feed 71, 73 and the liquid level of the reservoir vessel 31 are sent to a regulator for the valves.

To regulate the valves 65 through which the solvent is introduced into the extraction column via the feeds 61, 63, the flow rate through the feeds 61, 63 and the flow rate of the extract stream withdrawn are each sent to a regulator. The flow ratio is passed as a regulation parameter to the regulator for the feed 71, 73 for the liquid mixture to be separated.

FIG. 5 shows a schematic diagram of the process for preparing aromatic amine.

A nitroaromatic is supplied as the reactant to a reactor 83 via a reactant feed 81. When the aromatic amine to be prepared is aniline, the nitroaromatic used is nitrobenzene. Hydrogen is fed to the reactor 83 via a second feed 85. In the reactor 83, the nitroaromatic and the hydrogen are converted to the aromatic amine. The product mixture which forms is fed to a condenser 87. In the condenser 87, the aromatic amine and the water which forms in the reaction condense out. Unconverted hydrogen is recycled into the reactor 83 via the second feed 85. Hydrogen consumed is replaced via a hydrogen feed 89.

After the condensation, the remaining liquid mixture comprising water and aromatic amine is fed to a dewatering unit 91. An example of a suitable dewatering unit 91 is a liquid/liquid phase separation. In the dewatering unit 91, the liquid mixture comprising water and aromatic amine is separated into a first stream which comprises aromatic amine and residues, and a second stream which comprises water and residues of the aromatic amine.

The stream comprising aromatic amine and residues is fed to a distillation column 93. In the distillation column 93, the stream comprising the aromatic amine is separated into a top stream 95 which comprises aromatic amine as the pure product, and a bottom stream 97 which comprises residues.

The liquid mixture which comprises water and residues of the aromatic amine is sent to an inventive extraction column 1. The extraction column 1 is, for example, constructed as shown in FIG. 1. The nitroaromatic used to prepare the aromatic amine is fed to the extraction column 1 as the solvent via the first feed 9. The liquid mixture comprising water and residues of the aromatic amine is supplied via the second feed 11 in the lower region of the extraction column 1. An essentially water-comprising raffinate stream is drawn off via the second liquid outlet 15 at the top of the extraction column 1, and the extract stream comprising the nitroaromatic and the aromatic amine is withdrawn via the liquid outlet 13 at the bottom of the extraction column 1. The extract stream withdrawn in the liquid outlet 13 at the bottom of the extraction column 1 is recycled into the reactor 83 via a third feed 99. The recycling of the extract stream comprising the nitroaromatic and the aromatic amine into the reactor 83 and the further conduction of the aromatic amine through the remaining process steps increases the yield of aromatic amine. More particularly, it is unnecessary to separately process the extract stream withdrawn via the liquid outlet 13 at the bottom of the extraction column 1.

| List of reference numerals | |
|---|---|
| 1 | Extraction column |
| 3 | Dividing wall |
| 5 | first region |
| 7 | second region |
| 9 | first feed |
| 11 | second feed |
| 13 | Liquid outlet at the bottom |
| 15 | second liquid outlet |
| 17 | Top |
| 19 | Bottom |
| 21 | Phase boundary |
| 23 | Liquid level |
| 31 | Reservoir vessel |
| 33 | Pump |
| 35 | Valve |
| 37 | Regulating valve |
| 39 | Feed |
| 41 | Line |
| 43 | Line |
| 45 | Pump |
| 47 | Flow meter |
| 49 | Pump |
| 51 | Regulating valve |
| 53 | Fill level meter |
| 55 | Liquid level meter |
| 61 | Feed in the first region |
| 63 | Feed in the second region |
| 65 | Valve |
| 67 | Liquid display |
| 71 | Feed in the first region |
| 73 | Feed in the second region |
| 75 | Valve |
| 81 | Reactant feed |
| 83 | Reactor |
| 85 | second feed |
| 87 | Condenser |
| 89 | Hydrogen feed |
| 91 | Dewatering unit |
| 93 | Distillation column |
| 95 | Top stream |
| 97 | Bottom stream |
| 99 | third feed |

The invention claimed is:

1. A process for obtaining at least one aromatic amine from a liquid mixture comprising water and the at least one aromatic amine, the process comprising:
   extracting the at least one aromatic amine from the liquid mixture with at least one nitroaromatic in an extraction column to form raffinate stream comprising water and an extract stream comprising the at least one nitroaromatic and the aromatic amine,
   wherein a vertical dividing wall divides the extraction column into two regions, and
   if an amount of the liquid mixture for separation is less than a minimum cross sectional loading of the extraction column, the liquid mixture is fed only to one of the two regions of the extraction column.

2. The process of claim 1, wherein the dividing wall ends below a level of a liquid in the extraction column and above a first feed apparatus at the top of the extraction column.

3. The process of claim 1, wherein the dividing wall projects into a bottom liquid phase to be removed in the extraction column.

4. The process of claim 1,
   wherein a bottom liquid phase to be removed in the extraction column is an anhydrous extract phase comprising the at least one nitroaromatic and the at least one aromatic amine, and
   the raffinate stream is withdrawn at the top of the extraction column.

5. The process of claim 1, wherein a first feed opens into an upper region of the extraction column and a second feed opens at a lower end of the extraction column above the bottom in each of the regions divided by the dividing wall.

6. The process of claim 5, wherein the at least one nitroaromatic is added via the first feed in the upper region of the extraction column, and the liquid mixture is added via the second feed.

7. The process of claim 1, wherein the nitroaromatic is nitrobenzene and the aromatic amine is aniline.

8. A process for preparing an aromatic amine by catalytically hydrogenating a corresponding nitroaromatic, comprising:
   (a) converting a reaction mixture comprising the nitroaromatic and hydrogen With a heterogeneous catalyst in a reactor to obtain a product mixture comprising the aromatic amine, water and unconverted hydrogen in an equilibrium reaction,
   (b) removing the hydrogen from the product mixture,
   (c) dewatering the product mixture to obtain an anhydrous aromatic amine as a product, and a liquid mixture comprising water and residues of the aromatic amine,
   (d) separating the liquid mixture obtained in (c) in the process of claim 1 by extracting the at least one aromatic amine from the liquid mixture with a nitroaromatic to give a raffinate stream comprising water and an extract stream comprising the nitroaromatic and the aromatic amine.

9. The process of claim 8, wherein the nitroaromatic in (d) is the nitroaromatic used to prepare the aromatic amine in (a).

10. The process of claim 9, wherein the extract stream obtained in (d) is recycled into the reactor.

11. The process of claim 8, wherein the aromatic amine obtained in (c) is freed of residues by a distillation.

12. The process of claim 1,
   wherein an amount of the liquid mixture for separation is less than a minimum cross sectional loading of the extraction column, and
   wherein the extracting comprises feeding the liquid mixture only to one of the two regions of the extraction column.

* * * * *